| United States Patent [19] | [11] Patent Number: 4,760,091 |
| Carson et al. | [45] Date of Patent: Jul. 26, 1988 |

[54] METHOD OF CONTROLLING PHYTOPATHOGENIC FUNGUS

[75] Inventors: Chrislyn M. Carson, Antioch, Calif.; Peter P. McCann, Cincinnati, Ohio

[73] Assignee: The Dow Chemical Company, Midland, Mich.

[21] Appl. No.: 16,026

[22] Filed: Feb. 18, 1987

Related U.S. Application Data

[63] Continuation of Ser. No. 782,657, Oct. 1, 1985, abandoned.

[51] Int. Cl.$^4$ .................... A01N 37/12; A01N 37/44; A01N 37/06
[52] U.S. Cl. .................... 514/561; 514/549; 514/551
[58] Field of Search .................... 514/549, 551, 561

[56] References Cited

U.S. PATENT DOCUMENTS

| 4,134,918 | 1/1979 | Bey et al. | 564/240 |
| 4,267,374 | 5/1981 | Metcalf et al. | 564/240 |
| 4,323,704 | 4/1982 | Metcalf et al. | 562/561 |
| 4,325,961 | 4/1982 | Kollonitsch et al. | 514/400 |
| 4,413,141 | 11/1983 | Bey et al. | 562/561 |

OTHER PUBLICATIONS

Abstracts, Agrichemical Age, Apr. 1987, p. 8G.
Farm Chemicals Handbook, 1984, Meister Publishing Co., Willoughby, Ohio, cover page and pp. C-27, C-59, C-139 and C-214.

*Primary Examiner*—Leonard Schenkman
*Assistant Examiner*—Joseph A. Lipovsky
*Attorney, Agent, or Firm*—S. Preston Jones; Ronald G. Brookens

[57] ABSTRACT

This invention relates to a method of controlling phytopathogenic rust and smut fungi of the Uredinales order in a plant locus which comprises applying a fungicidally effective amount of an ornithine decarboxylase inhibitor.

14 Claims, No Drawings

METHOD OF CONTROLLING PHYTOPATHOGENIC FUNGUS

This application is a continuation of Ser. No. 06/782,657 filed Oct. 1, 1985; now abandoned.

This invention relates to the method of controlling phytopathogenic fungi utilizing certain compounds having ornithine decarboxylase inhibiting properties, and to the agricultural compositions for facilitating this use.

More particularly this invention relates to the use of known ornithine decarboxylase inhibitors of the formula.

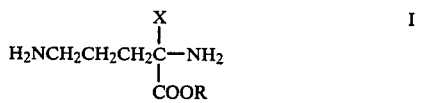

the 3,4-dehydro analogs thereof, the agriculturally acceptable salts thereof, wherein X is —$CFH_2$ or —$CF_2H$, R is H or $C_{1-18}$ alkyl, as active compounds in the control of phytopathogenic fungi, particularly rusts and smuts.

The active ornithine decarboxylase (ODC) inhibitors of formula I include the mono and difluoromethyl ornithines, i.e., α-fluoromethyl ornithine (α-MFMO), α-difluoromethylornithine (α-DFMO), the mono and difluoromethyl dehydro ornithine, (i.e. De-MFMO and De-DFMO of the subgeneric formula IA.

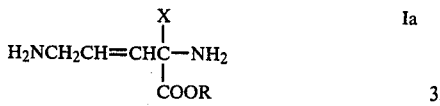

These ODC inhibitors have been described in U.S. Pat. Nos. 4325961 and 4413141. The preferred esters are those wherein R represents methyl and ethyl but also embrace all the straight and branched manifestations of the remaining $C_{3-18}$ alkyl radicals. Preferred salts are the alkaline earth and alkali metal salts.

The phytopathogenic fungi controlled by the ornithine decarboxylase inhibitors of formula I include the rust fungi belonging to the Uredinales order and the smuts of the order Ustilaginales, each group being very closely related and are of similar economic importance. Although this invention is of a generic nature, the three most important families of rust fungi embraced by this invention are Puccineaceae, Melampsoracea and Coleosporiaceae.

Puccinia, Uromyces, Phragmidium and Gymnosporangium genera belong to the Puccineaceae family. These genera along with some others of the other families belong to the economically most important rust fungi. Of the about 200 or more species and subspecies of rust fungi attacking agricultural crops, about 120 belong to the Puccinia and about 40 to the Uromyces genus. Rusts are highly host—or even host organ-specific and many plant species are therefore infested by various specific rusts. Thus, wheat is attacked by 3 main Puccinia species (*P. triticina;* syn. *P. recondita* or *P. rubigo-vera*) the leaf or brown rust, *P. glumarum*-yellow or stripe rust and *P. graminis* (stem rust). However, brown rust infecting corn is induced by another species (*Puccinia maydis;* syn. *P. sorghi*).

Some *Puccinia* species developed subspecies specific for various cereals, grasses, and other crops. The most important rust diseases are those induced by Puccinia species in the main crops of the world. Most Uromyces species attack legumes (both annual and perennial) and some of them also grasses and other crops. Bean-infecting Uromyces are known under the names: *U. phaseoli, U. phaseolorum,* and *U. appendiculatus.* The disease induced by these species in bean is of lesser agricultural importance than other pea diseases but are still of importance. Specific rust genera belonging to Melampsoracea and Calosporeacea include Melampsora, cronartrum, Caleosponium, as well as other genera belonging to the two rust families.

Chemical toxicants used for the control of fungal foliage diseases fall generally into three (3) major categories: (1) protectant agents, (2) systemic agents and (3) curative or therapeutic agents. Protectant agents act principally as residues for toxicants that are inhibitory to spore germination on the host surface. Systemic agents penetrate and move inside the host to act against invading pathogens. Curative agents act within the host to alter the fungal disease process thereby aiding the host to tolerate or recover from the adverse effects of pathogenesis.

Principal limitations with protectant agents for the control of cereal rusts are the proper timing of applications, incomplete coverage of host surfaces with aerial applications and the rapid loss of protectant agent deposits with rain. The uptake, transport and eradicant characteristics of systemic agents in the host partially compensate for the limitations of protectant agents. The principal problem with systemic agents is the maintenance of an effective non-phytotoxic dose within the host without leaving undesirable residues in the harvested wheat. No curative agents are known for controlling the rust and smut fungi, particularly cereal and bean infecting rusts.

The active compounds of the present invention offer unique advantages in the treatment of cereal and bean rusts by (1) exhibiting protectant and curative activity and (2) being effective when applied to the soil, seed and foliage. These unique properties provide a flexibility in the timing of applications not currently available. Therefore, in accordance with the present invention, rusts and smuts (of the above described families) are effectively controlled in susceptible cereal, bean and other economic crops by application of an effective amount of the ornithine decarboxylase inhibitors of formula I α-difluoromethyl ornithine (DFMO), α-monofluoromethyl ornithine (MFMO), dehydro-monofluoromethyl ornithine (DeMFMO) or salts of these compounds. Mixtures of these compounds can also be used. The compounds can be applied to the soil, to the seeds or to the foliage of growing plants.

Still more particularly, *Puccinia recondita,* commonly known as wheat leaf rust, and *Puccinia graminis tritici,* commonly known as wheat stem rust, are effectively controlled in susceptible wheat crops by application of an effective amount of DFMO, MFMO, DeMFMO, salts thereof or mixtures thereof. These compounds are conveniently applied to wheat seeds and/or to the foliage of growing wheat plants and when used herein, the term "cereal rust" is meant to encompass *Puccinia recondita, Puccinia hordei. Puccinia striiformis* and *Puccinia graminis,* also known as (AKA), wheat leaf rust, brown rust, stripe rust and stem rust, respectively. The terms "cereal" and "cereal crops" are meant to encompass the cereal crop which is inflicted with a particular cereal rust, such as, for example, wheat (stripe rust, wheat stem rust and wheat leaf rust) and barley (brown rust). The term "controlling cereal rust" is meant to encompass the biological activity the active compounds exhibit against cereal rusts including protectant activity and curative activity.

When used herein, the term "wheat rust" is meant to encompass both wheat leaf rust and wheat stem rust. The term "controlling wheat rust" is meant to encompass the biological activity the active compounds exhibit against wheat rust including protectant activity and curative activity. Agriculturally acceptable salts of the above compounds, such as, alkaline earth metal and alkali metal salts, are also contemplated by the present invention.

In practicing the present invention, DFMO, MFMO, DeMFMO, salts thereof or mixtures thereof, are applied to suceptible cereal seeds, foliage of cereal plants or to their habitat in the soil in amounts effective to control cereal rusts.

For all such uses, unmodified active compounds of the present invention can be employed. However, the present invention embraces the use of a fungicidally-effective amount of the active compounds in composition form with an inert material known in the art as an agricultural adjuvant or carrier in solid or liquid form. Such adjuvants or carriers must not be phytotoxic to cereal crops or seeds particularly at the concentration employed in applying the composition in attempting to control cereal rust.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituents of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid fungicidal formulations are similarly well known to the skilled artisan.

The concentration of the active compounds in solid or liquid compositions generally is from about 0.003 to about 95 percent by weight or more. Concentrations from about 0.05 to about 50 percent by weight are often employed. In compositions to be employed as concentrates, the active compound can be present in a concentration from about 5 to about 98 weight percent, preferably 15-50 weight percent. The compositions containing the active compounds can also contain other compatible additaments, for example, phytotoxicants, plant growth regulators, pesticides and the like which are suitable for application to cereal crops. The present compositions can be applied by the use of power dusters, boom and hand sprayers, spray dusters and by other conventional means. The compositions can also be applied from airplanes as a dust or spray since the active ingredients are effective at very low application rates.

The exact rate to be applied is dependent not only on the specific active compound being applied, but also on the particular treatment desired (e.g., seed, soil or foliage,) the particular cereal crop being treated, climatic conditions, severity of the cereal rust infection and the like. Thus, it is also to be understood that all of the active compounds of the present invention and compositions containing the same may not be equally effective at similar concentrations or against the same fungal species.

Using standard agricultural testing techniques and standard assay methodology for ornithine decarboxylase inhibiting properties, one skilled in the art can readily determine an effective rate. In foliar treatments, the active compounds of the present invention are usually applied at an approximate rate of from about 0.06 to about 1.0 pounds/acre, a rate of from about 0.125 to about 0.5 pounds/acre being preferred and a rate of from about 0.25 to about 0.375 pounds/acre being particularly preferred.

In seed treatments, the active compounds of the present invention are usually applied at an approximate rate of from about 1 to about 16 ounces per 100 pounds of seed, a rate of from about 2 to about 16 ounces per 100 pounds of seed being preferred and a rate of from about 4 to about 8 ounces per 100 pounds of seed being particularly preferred.

In soil treatments, the active compounds of the present invention are usually applied at an approximate rate of from about 0.04 to about 0.57 pounds/acre, a rate of from about 0.14 to about 0.57 pounds/acre being preferred and a rate of from about 0.14 to about 0.28 pounds/acre being particularly preferred.

A typical solid composition is formulated by dry milling the active compound with BARDEN® clay. This solid formulation or dust can contain the active compound in amounts of from about 1 to about 25 percent by weight or more if desired. The dust is suitable for application to cereal seeds prior to planting.

A typical liquid composition is formulated by dissolving the active compound in a mixture of water and isopropanol (80:20 water/isopropanol ratio) containing a surfactant. This liquid formulation can contain the active compound in amounts of from about 0.001 to about 25 percent by weight or more if desired. The aqueous formulation is suitable for application to cereal foliage or application as a seed drench.

The active compounds of the present invention contain an optically active center and can exist in optically active stereoisomeric forms such as dextrorotatory and levorotatory isomeric forms. The various mixtures and racemates of the above isomers are within the scope of the present invention.

In a preferred embodiment, one or more active compounds are applied to susceptible wheat seeds, foliage of wheat plants and/or to their habitat in the soil in amounts effective to control wheat rust.

The following examples illustrate the practice of the present invention but should not be construed as limiting its scope.

EXAMPLE 1

Protectant Activity

A 10,000 ppm concentrate of α-difluoromethyl ornithine (DFMO) in water was prepared. From this concentrate, dilutions of 1200, 300 and 75 ppm DFMO in aqueous solutions containing 20% by volume isopropanol and 250 ppm TRITON® X-100 brand surfactant were prepared. Similar dilutions were prepared with α-monofluoromethyl dehydro ornithine (DeMFMO). The active compounds were applied as foliar sprays to one week old wheat plants (var. Sonora). Foliar applications were made by spraying the foliage to run-off with a 2 ml glass CORNWALL ® syringe fitted with TEE-JET ® TN-3 spray nozzle. Four (4) days later the plants were inoculated with wheat leaf rust (*Puccinia recondita*) uredospores. The plants were incubated at 65° F. at 100% relative humidity in a bioclimatic chamber for one (1) day and then placed in a greenhouse. The protectant activity of the compounds was evaluated by estimating the percent control of wheat leaf rust relative to untreated but inoculated control plants when the lesions of the control plants were fully erumpent (~7-10 days). The results are listed below:

| Active Compound | % Control at rate, ppm | | |
|---|---|---|---|
| | 1200 | 300 | 75 |
| DFMO | 100 | 75 | 0 |
| DeMFMO | 100 | 100 | 75 |

EXAMPLE 2

Curative Activity

The 10,000 ppm concentrates of DFMO and DeMFMO described in Example 1 were used to prepare dilutions of 1,000 and 100 ppm of active compound in aqueous solutions containing 20% by volume isopropanol and 250 ppm TRITON ® X-100 brand surfactant. The active compounds were applied (one day post inoculation) as foliar sprays to 10 day old greenhouse grown wheat plants (var. Sonora) which were irreversibly infected with wheat leaf rust (*Puccinia recondita*). The curative activity of the compounds was evaluated 8 days later when the lesions of inoculated but untreated control plants were fully erumpent by estimating the percent control relative to the control plants. The results are listed below:

| Active Compound | % Control at rate, ppm | |
|---|---|---|
| | 1000 | 100 |
| DFMO | 100 | 100 |
| DeMFMO | 100 | 100 |

EXAMPLE 3

Seed Treatment Activity

Two dust compositions for seed treatment were formulated by dry milling (a) 10 parts by weight of monofluoromethyl ornithine (MFMO) with 90 parts by weight BARDEN ® clay and (b) 10 parts by weight -monofluoromethyl dehydro ornithine (DeMFMO) with 90 parts by weight BARDEN ® clay. The dusts containing the active compounds were then thoroughly mixed with seeds of var. Sonora wheat at rates equivalent to 8, 4, 2 and 1 ounce active compound/cwt of seed. For each treatment, 20 seeds were placed in 2 inch pots of sterile sandy soil and covered with 0.5 inch of sterile soil. Each treatment was replicated. The pots were then watered and placed in a greenhouse. One week later, the emerged seedlings were inoculated with freshly harvested uredospores of wheat leaf rust (*Puccinia recondita*) and placed in a bioclimatic chamber at 65° F. at 100% relative humidity for 24 hours, after which the seedlings were returned to the greenhouse. The seed treatment activity of the active compounds was evaluated 10 days later by estimating the percent control of wheat leaf rust relative to untreated but inoculated control plants. The results are listed below as the average of the replicate treatments.

| Active Compound | % Control of wheat leaf rust at rate (oz/cwt) | | | |
|---|---|---|---|---|
| | 8 | 4 | 2 | 1 |
| DeMFMO | 100 | 99 | 0 | 0 |
| MFMO | 100 | 100 | 25 | 0 |

EXAMPLE 4

Curative and Protective Activity of DFMO

DFMO, at concentrations of 1200, 300 and 75 ppm, was evaluated for protectant and curative activity against leaf rust on mature flag leaf stage wheat plants employing substantially the same procedures described in Examples 1 and 2 respectively. The results are listed below:

| Percent Control of Leaf Rust | | | | | |
|---|---|---|---|---|---|
| Protectant Activity | | | Curative Activity | | |
| 1200 ppm | 300 ppm | 75 ppm | 1200 ppm | 300 ppm | 75 ppm |
| 100% | 100% | 85% | 100% | 100% | 50% |

EXAMPLE 5

Curative Activity Against Leaf Rust and Stem Rust

DFMO and DeMFMO, at concentrations of 1000 ppm and 100 ppm, were evaluated for curative activity against both wheat leaf rust and wheat stem rust employing substantially the same procedures described in Example 2. The results are listed below:

| Compound | % Control Leaf Rust | | % Control Stem Rust | |
|---|---|---|---|---|
| | 1000 ppm | 100 ppm | 1000 ppm | 100 ppm |
| DFMO | 100% | 100% | 99% | 50% |
| DeMFMO | 100% | 95% | 99% | 50% |

EXAMPLE 6

Seed Drench Test

About 20 wheat seeds were sown on sterile sandy soil in a 2 inch plastic pot. The seeds were covered with ½ inch of vermiculite and, prior to watering, were drenched with 40 ml of an aqueous solution containing 100 ppm DFMO. Identical treatments were conducted with MFMO and DeMFMO being employed as the active compounds. The plants were then placed in a greenhouse under conditions conducive to growth of the plants. When the wheat reached a height of 3-5 inches, the emergent foliage was inoculated with freshly harvested uredospores of wheat leaf rust. The inoculated plants were incubated in a biochamber for 1 day (65° F; 100% relative humidity), then returned to the greenhouse. The seed drench activity of the active compounds was evaluated when the lesions of inoculated but untreated control plants were fully erumpent by comparing percent control of wheat leaf rust relative to the control plants. The results are listed below:

| Active Compound | % Control Wheat Leaf Rust |
|---|---|
| DFMO | 90 |
| MFMO | 100 |

| -continued | |
|---|---|
| Active Compound | % Control Wheat Leaf Rust |
| DeMFMO | 100 |

EXAMPLE 7

Foliar Residuality (Protectant Activity)

Substantially the same procedures described in Example 1 were repeated except that the plants were inoculated at the 5th, 7th, 10th and 12th day post treatment. The active compounds tested wee DFMO, MFMO and DeMFMO, all at both 1200 ppm and 300 ppm. The results are listed below:

| | % Control leaf rust on plants* inoculated at day indicated post treatment | | | |
|---|---|---|---|---|
| Treatment, Rate (ppm) | Day 5 | Day 7 | Day 10 | Day 12 |
| MFMO, 1200 ppm | 100 | 100 | 100 | 100 |
| MFMO, 300 ppm | 99 | 100 | 100 | 25 |
| DFMO, 1200 ppm | 100 | 100 | 90 | 50 |
| DFMO, 300 ppm | 99 | 25 | 25 | 0 |
| DeMFMO, 1200 ppm | 100 | 100 | 50 | 75 |
| DeMFMO, 300 ppm | 95 | 50 | 25 | 0 |

*Mature, Flag Leaf Stage Sonora Wheat

EXAMPLE 8

Curative Activity

Substantially the same procedures as described in Example 2 were repeated except that the plants were treated on the 3rd, 4th and 5th day inoculation. The active compounds tested were DFMO, MFMO and DeMFMO, all at both 1200 ppm and 300 ppm. The results are listed below:

| | % Control leaf rust on plants* treated at day indicated post inoculation | | |
|---|---|---|---|
| Treatment, Rate (ppm) | Day 3 | Day 4 | Day 5 |
| MFMO, 1200 ppm | 100 | 100 | 25 |
| MFMO, 300 ppm | 99 | 99 | 0 |
| DFMO, 1200 ppm | 100 | 99 | 0 |
| DFMO, 300 ppm | 90 | 75 | 0 |
| DeMFMO, 1200 ppm | 100 | 100 | 25 |
| DeMFMO, 300 ppm | 100 | 100 | 0 |

*Mature, Flag Leaf Stage Sonora Wheat

EXAMPLE 9

Seed Treatment

Substantially the same procedures described in Example 3 were repeated except that dusts containing 20% by weight active ingredient were employed. DFMO, MFMO and DeMFMO were evaluated for effectiveness of a seed treatment for the control of foliar wheat leaf rust. The results are listed below:

| | % Control of wheat leaf rust indicated rate; (ox/cwt) | | | |
|---|---|---|---|---|
| Treatment | 16 | 8 | 4 | 2 |
| DeMFMO | 100 | 100 | 90 | 90 |
| MFMO | 100 | 100 | 100 | 100 |
| DFMO | 100 | 100 | 75 | 75 |

EXAMPLE 10

Field Trial

A small field trial was conducted in Walnut Creek, Calif., to establish curative and protectant activity of DFMO under field conditions. DFMO was applied at rates equivalent to 1 lb and 0.25 lb per acre to mature flag leaf stage Sonora wheat. The foliar spray was applied with a portable track sprayer using a volume equivalent to 20 gallons/acre. The track sprayer was fitted with a TEE-JET ® 8002E spray nozzle, pressurized to 40 psi and run at a speed of 2 mph at a height of 10 inches above plant tops to give a swath of approximately 18 inches with an 80° spray angle. In this field trial the rows of wheat were spaced one foot apart with 3 rows/treatment. Border rows were left between treatments. Polyethylene cages (4'×5'×3') were placed over treated areas immediately after inoculation with wheat leaf rust to allow the relative humidity to reach 100% during the 24 hour incubation period. If the temperature exceeded 95° F. in the cage then that treatment was aborted. The plots were irrigated 2 days prior to inoculation to assure sufficient moisture for humidity build-up. The curative test plots, replicated twice, were conducted by application of DFMO one day post-inoculation. The protectant test plots, replicated 3 times, were conducted by application of DFMO 4 days pre-inoculation. All treatments gave complete control of leaf rust under the conditions tested. Hypersensitive type flecking was noted in both curative and protectant treatments.

EXAMPLE 11

Curative Activity

Substantially the same procedures as described in Example 2 were repeated except the plants were treated on the 4th day post-inoculation with wheat stem rust. The active compounds tested were DFMO, MFMO and DeMFMO, all at 1200 ppm, 300 ppm and 75 ppm. The results are listed below:

| | % Control of wheat stem rust at indicated rate, ppm | | |
|---|---|---|---|
| Treatment | 1200 ppm | 300 ppm | 75 ppm |
| MFMO | 100 | 100 | 100 |
| DFMO | 100 | 100 | 100 |
| DeMFMO | 100 | 100 | 100 |

EXAMPLE 12

Protectant Activity

Substantially the same procedures as described in Example 1 were repeated except the wheat plants were inoculated with wheat stem rust on the 4th, 6th or 7th day after treatment with the active compound. The active compounds tested were MFMO and DFMO, both at 1200 ppm, 300 ppm and 75 ppm. The results are listed below:

| | % Control wheat stem rust inoculated at day indicated post treatment | | |
|---|---|---|---|
| Treatment, rate (ppm) | Day 4 | Day 6 | Day 7 |
| MFMO, 1200 ppm | 100 | 100 | 100 |
| MFMO, 300 ppm | 100 | 100 | 0 |
| MFMO, 75 ppm | 100 | 100 | 0 |

-continued

| Treatment, rate (ppm) | % Control wheat stem rust inoculated at day indicated post treatment | | |
|---|---|---|---|
| | Day 4 | Day 6 | Day 7 |
| DFMO, 1200 ppm | 100 | 50 | 75 |
| DFMO, 300 ppm | 100 | 0 | 0 |
| DFMO, 75 ppm | 100 | 0 | 0 |

In similar operations, mixtures of the present compounds, i.e., DFMO, MFMO, DeMFMO and salts thereof, provide excellent curative protectant and seed treatment activity against the various cereal rusts described herein.

We claim:

1. A method of controlling phytopathogenic rust and smuts of the Uredinales order in a plant locus comprising applying to said locus a fungicidally effective amount of an ornithine decarboxylase inhibitor of the formula

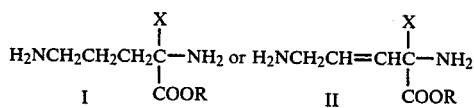

and the agriculturally acceptable salts thereof wherein R is hydrogen or $C_{1-18}$ alkyl and X is $-CFH_2$ or $-CF_2H$.

2. A method of claim 1 wherein the Uredinales fungi are of the families Puccineaceae, Melampsoracea or Coleosporiaceae.

3. A method of claim 2 wherein the fungi are of the Puccineaceae family.

4. A method of claim 3 wherein the fungi are of the Puccinia genera.

5. A method of claim 3 wherein the fungi are of the *Uromyces genera*.

6. A method of claim 1 wherein the plant is corn and the fungus is of the *Puccinia genera*.

7. A method of claim 1 wherein the plant is wheat and the fungus is of the *Puccinia genera*.

8. A method of claim 7 wherein the fungus is wheat leaf rust *Puccinia triticina*.

9. A method of claim 7 wherein the fungus is wheat stem rust or *Puccinia graminis*.

10. A method of claim 7 wherein the fungus is *Puccinia glumarum*.

11. A method of claim 1 wherein the plant is a legume and the fungus is of the *Uromyces genera*.

12. A method of claim 1 wherein the ornithine decarboxylase inhibitor is α-difluoromethyl ornithine.

13. A method of claim 11 wherein the bean-infecting Uromyces is of *U. phaseoli, U. phaseolorum* or *U. appendiculatus*.

14. A method of claim 6 wherein the corn-infecting fungus is *Puccinia maydis*.

* * * * *